US009241735B2

(12) United States Patent
Kick et al.

(10) Patent No.: US 9,241,735 B2
(45) Date of Patent: Jan. 26, 2016

(54) EXPANDABLE PERCUTANEOUS SHEATH

(75) Inventors: George F. Kick, Casa Grande, AZ (US);
Thanh Van Nguyen, Irvine, CA (US);
Samuel M. Shaolian, Newport Beach, CA (US)

(73) Assignee: Onset Medical Corporation, Irvine, CA (US)

( * ) Notice: Subject to any disclaimer, the term of this patent is extended or adjusted under 35 U.S.C. 154(b) by 1476 days.

(21) Appl. No.: 10/728,728

(22) Filed: Dec. 5, 2003

(65) Prior Publication Data
US 2005/0124937 A1    Jun. 9, 2005

(51) Int. Cl.
*A61M 5/178* (2006.01)
*A61B 17/34* (2006.01)
*A61M 25/06* (2006.01)
*A61M 31/00* (2006.01)
*A61M 25/00* (2006.01)

(52) U.S. Cl.
CPC ......... *A61B 17/3439* (2013.01); *A61B 17/3417* (2013.01); *A61B 17/3421* (2013.01); *A61M 25/0662* (2013.01); *A61M 25/0668* (2013.01); *A61M 31/005* (2013.01); *A61M 2025/0024* (2013.01); *A61M 2025/0681* (2013.01)

(58) Field of Classification Search
CPC ........... A61B 17/3417; A61B 17/3421; A61B 2017/3425; A61B 17/3431; A61B 2017/3433; A61B 17/3439; A61M 2025/0024; A61M 25/0668; A61M 2025/0681; A61M 25/0662
USPC ............................. 606/192; 604/104, 164.04
See application file for complete search history.

(56) References Cited

U.S. PATENT DOCUMENTS

| 319,296 | A | 6/1885 | Molesworth |
| 668,879 | A | 2/1901 | Miller |
| 1,213,001 | A | 1/1917 | Philips |
| 1,248,492 | A | 12/1917 | Hill |
| 2,042,900 | A | 6/1936 | James |
| 2,548,602 | A | 4/1948 | Greenburg |
| 3,509,883 | A | 5/1970 | Dibelius |
| 3,545,443 | A | 12/1970 | Ansari |
| 3,742,958 | A | 7/1973 | Rundles |
| 3,789,852 | A | 2/1974 | Kim et al. |

(Continued)

FOREIGN PATENT DOCUMENTS

EP    0177177    4/1986
EP    0 249 456  12/1987

(Continued)

OTHER PUBLICATIONS

International Search Report mailed Oct. 28, 2005 for International Application No. PCT/US2004/040651 filed Dec. 3, 2004.

(Continued)

*Primary Examiner* — Kathleen Holwerda
*Assistant Examiner* — Sarah Simpson
(74) *Attorney, Agent, or Firm* — Inskeep IP Group, Inc.

(57) ABSTRACT

Disclosed is an expandable percutaneous sheath, for introduction into the body while in a first, low cross-sectional area configuration, and subsequent expansion to a second, enlarged cross-sectional configuration. The sheath is maintained in the first, low cross-sectional configuration by a tubular restraint. In one application, the sheath is utilized to provide access for a diagnostic or therapeutic procedure such as percutaneous nephrostomy or urinary bladder access.

19 Claims, 10 Drawing Sheets

(56) References Cited

U.S. PATENT DOCUMENTS

| | | | | |
|---|---|---|---|---|
| 3,902,492 A | | 9/1975 | Greenhalgh | |
| 4,018,230 A | | 4/1977 | Ochiai et al. | |
| 4,141,364 A | | 2/1979 | Schultze | |
| 4,338,942 A | | 7/1982 | Fogarty | |
| 4,401,433 A | | 8/1983 | Luther | |
| 4,411,655 A | | 10/1983 | Schreck | |
| 4,451,256 A | | 5/1984 | Weikl et al. | |
| 4,479,497 A | | 10/1984 | Fogarty et al. | |
| 4,581,025 A | | 4/1986 | Timmermans | |
| 4,589,868 A | | 5/1986 | Dretler | |
| 4,601,713 A | | 7/1986 | Fuqua | |
| 4,610,688 A | | 9/1986 | Silvestrini et al. | |
| 4,636,346 A | | 1/1987 | Gold et al. | |
| 4,650,466 A | | 3/1987 | Luther | |
| 4,710,181 A | | 12/1987 | Fuqua | |
| 4,716,901 A | | 1/1988 | Jackson et al. | |
| 4,738,666 A | * | 4/1988 | Fuqua | 604/514 |
| 4,739,762 A | | 4/1988 | Palmaz | |
| 4,772,266 A | | 9/1988 | Groshong | |
| 4,790,817 A | | 12/1988 | Luther | |
| 4,798,193 A | | 1/1989 | Giesy et al. | |
| 4,846,791 A | | 7/1989 | Hattler et al. | |
| 4,865,593 A | | 9/1989 | Ogawa et al. | |
| 4,869,717 A | | 9/1989 | Adair | |
| 4,884,573 A | | 12/1989 | Wijay et al. | |
| 4,888,000 A | | 12/1989 | McQuilkin et al. | |
| 4,896,669 A | | 1/1990 | Bhate et al. | |
| 4,898,591 A | | 2/1990 | Jang et al. | |
| 4,899,729 A | | 2/1990 | Gill et al. | |
| 4,921,479 A | | 5/1990 | Grayzel | |
| 4,954,126 A | | 9/1990 | Wallsten | |
| 4,955,895 A | | 9/1990 | Sugiyama et al. | |
| 4,972,827 A | | 11/1990 | Kishi et al. | |
| 4,984,564 A | | 1/1991 | Yuen | |
| 4,986,830 A | | 1/1991 | Owens et al. | |
| 5,011,488 A | | 4/1991 | Ginsburg et al. | |
| 5,035,686 A | | 7/1991 | Crittenden et al. | |
| 5,045,056 A | | 9/1991 | Behl | |
| 5,057,092 A | | 10/1991 | Webster, Jr. | |
| 5,059,183 A | * | 10/1991 | Semrad | 604/158 |
| 5,066,285 A | | 11/1991 | Lundquist et al. | |
| 5,073,166 A | | 12/1991 | Parks et al. | |
| 5,078,736 A | | 1/1992 | Behl | |
| 5,092,839 A | | 3/1992 | Kipperman | |
| 5,098,393 A | | 3/1992 | Amplatz et al. | |
| 5,100,388 A | | 3/1992 | Behl et al. | |
| 5,108,413 A | | 4/1992 | Moyers | |
| 5,108,416 A | | 4/1992 | Ryan et al. | |
| 5,112,304 A | | 5/1992 | Barlow et al. | |
| 5,112,308 A | | 5/1992 | Olsen et al. | |
| 5,116,318 A | | 5/1992 | Hillstead | |
| 5,122,122 A | | 6/1992 | Allgood | |
| 5,139,511 A | | 8/1992 | Gill et al. | |
| 5,147,316 A | | 9/1992 | Castillenti | |
| 5,158,545 A | * | 10/1992 | Trudell et al. | 604/509 |
| 5,163,903 A | | 11/1992 | Crittenden et al. | |
| 5,176,659 A | | 1/1993 | Mancini | |
| 5,183,464 A | | 2/1993 | Dubrul et al. | |
| 5,188,602 A | | 2/1993 | Nichols | |
| 5,201,756 A | | 4/1993 | Horzewski et al. | |
| 5,222,938 A | | 6/1993 | Behl | |
| 5,222,971 A | | 6/1993 | Willard et al. | |
| 5,234,425 A | | 8/1993 | Fogarty et al. | |
| 5,250,025 A | * | 10/1993 | Sosnowski et al. | 604/506 |
| 5,250,033 A | | 10/1993 | Evans et al. | |
| 5,256,150 A | | 10/1993 | Quiachon et al. | |
| 5,275,611 A | | 1/1994 | Behl | |
| 5,279,553 A | | 1/1994 | Winkler et al. | |
| 5,295,994 A | | 3/1994 | Bonutti | |
| 5,312,360 A | | 5/1994 | Behl | |
| 5,312,417 A | | 5/1994 | Wilk | |
| 5,316,360 A | | 5/1994 | Feikma | |
| 5,318,588 A | | 6/1994 | Horzewski et al. | |
| 5,320,611 A | | 6/1994 | Bonutti et al. | |
| 5,324,261 A | | 6/1994 | Amundson et al. | |
| 5,346,503 A | | 9/1994 | Chow et al. | |
| 5,380,304 A | | 1/1995 | Parker | |
| 5,392,766 A | | 2/1995 | Masterson et al. | |
| 5,395,341 A | | 3/1995 | Slater | |
| 5,395,349 A | | 3/1995 | Quiachon et al. | |
| 5,407,430 A | | 4/1995 | Peters | |
| 5,409,469 A | | 4/1995 | Schaerf | |
| 5,431,676 A | | 7/1995 | Dubrul et al. | |
| 5,433,708 A | | 7/1995 | Nichols et al. | |
| 5,447,503 A | | 9/1995 | Miller | |
| 5,454,790 A | | 10/1995 | Dubrul | |
| 5,460,170 A | | 10/1995 | Hammerslag | |
| 5,507,767 A | | 4/1996 | Maeda et al. | |
| 5,514,091 A | | 5/1996 | Yoon | |
| 5,514,236 A | | 5/1996 | Avellanet et al. | |
| 5,527,336 A | | 6/1996 | Rosenbluth | |
| 5,540,658 A | | 7/1996 | Evans et al. | |
| 5,542,928 A | | 8/1996 | Evans et al. | |
| 5,549,635 A | | 8/1996 | Solar | |
| 5,571,089 A | | 11/1996 | Crocker | |
| 5,573,509 A | | 11/1996 | Thornton | |
| 5,573,517 A | | 11/1996 | Bonutti et al. | |
| 5,573,520 A | | 11/1996 | Schwartz | |
| 5,647,857 A | | 7/1997 | Anderson et al. | |
| 5,657,963 A | | 8/1997 | Hincliffe et al. | |
| 5,662,614 A | | 9/1997 | Edoga | |
| 5,674,240 A | | 10/1997 | Bonutti et al. | |
| 5,700,253 A | | 12/1997 | Parker | |
| 5,702,373 A | | 12/1997 | Samson | |
| 5,709,713 A | | 1/1998 | Evans et al. | |
| 5,713,867 A | | 2/1998 | Morris | |
| 5,738,667 A | | 4/1998 | Solar | |
| 5,766,203 A | | 6/1998 | Imran et al. | |
| 5,776,141 A | * | 7/1998 | Klein et al. | 623/1.11 |
| 5,810,776 A | * | 9/1998 | Bacich et al. | 604/131 |
| 5,817,100 A | | 10/1998 | Igaki | |
| 5,846,251 A | | 12/1998 | Hart | |
| 5,868,719 A | | 2/1999 | Tsukernik | |
| 5,868,779 A | | 2/1999 | Ruiz | |
| 5,885,217 A | | 3/1999 | Gisselberg et al. | |
| 5,888,196 A | | 3/1999 | Bonutti | |
| 5,897,557 A | | 4/1999 | Chin et al. | |
| 5,902,282 A | | 5/1999 | Balbierz | |
| 5,908,435 A | | 6/1999 | Samuels | |
| 5,916,145 A | | 6/1999 | Chu et al. | |
| 5,922,019 A | | 7/1999 | Hankh et al. | |
| 5,961,499 A | * | 10/1999 | Bonutti et al. | 604/272 |
| 5,964,730 A | | 10/1999 | Williams et al. | |
| 5,971,938 A | | 10/1999 | Hart et al. | |
| 5,997,508 A | | 12/1999 | Lunn et al. | |
| 6,030,364 A | * | 2/2000 | Durgin et al. | 604/164.01 |
| 6,056,718 A | | 5/2000 | Funderburk et al. | |
| 6,063,056 A | | 5/2000 | Engelberg | |
| 6,080,174 A | | 6/2000 | Dubrul et al. | |
| 6,090,072 A | | 7/2000 | Kratoska et al. | |
| 6,120,480 A | | 9/2000 | Zhang et al. | |
| 6,123,689 A | | 9/2000 | To et al. | |
| 6,168,579 B1 | | 1/2001 | Tsugita | |
| 6,183,443 B1 | | 2/2001 | Kratoska et al. | |
| 6,187,000 B1 | | 2/2001 | Davison et al. | |
| 6,197,016 B1 | | 3/2001 | Fourkas et al. | |
| 6,228,052 B1 | | 5/2001 | Pohndorf | |
| 6,248,116 B1 | | 6/2001 | Chevillon et al. | |
| 6,280,452 B1 | | 8/2001 | Mears | |
| 6,293,909 B1 | | 9/2001 | Chu et al. | |
| 6,312,443 B1 | | 11/2001 | Stone | |
| 6,358,238 B1 | | 3/2002 | Sherry | |
| 6,443,979 B1 | | 9/2002 | Stalker et al. | |
| 6,447,540 B1 | | 9/2002 | Fontaine et al. | |
| 6,471,684 B2 | | 10/2002 | Dulak et al. | |
| 6,494,860 B2 | | 12/2002 | Rocamora et al. | |
| 6,494,893 B2 | | 12/2002 | Dubrul et al. | |
| 6,517,551 B1 | | 2/2003 | Driskill | |
| 6,524,268 B2 | | 2/2003 | Hayner et al. | |
| 6,524,320 B2 | | 2/2003 | DiPoto | |
| 6,530,902 B1 | | 3/2003 | Jonkman | |
| 6,537,247 B2 | * | 3/2003 | Shannon | 604/103.05 |
| 6,582,395 B1 | | 6/2003 | Burkett et al. | |
| 6,613,038 B2 | | 9/2003 | Bonutti et al. | |

(56) References Cited

U.S. PATENT DOCUMENTS

| | | | |
|---|---|---|---|
| 6,613,062 | B1 | 9/2003 | Leckrone et al. |
| 6,616,678 | B2 * | 9/2003 | Nishtala et al. ............... 606/198 |
| 6,638,268 | B2 | 10/2003 | Niazi |
| 6,679,902 | B1 | 1/2004 | Boyle et al. |
| 6,692,462 | B2 | 2/2004 | Mackenzie et al. |
| 6,692,482 | B2 | 2/2004 | Heller et al. |
| 6,706,017 | B1 | 3/2004 | Dulguerov |
| 6,808,520 | B1 * | 10/2004 | Fourkas et al. ............... 604/526 |
| 6,827,683 | B2 | 12/2004 | Otawara |
| 6,951,555 | B1 | 10/2005 | Suresh et al. |
| 7,033,369 | B2 | 4/2006 | Davison et al. |
| 7,056,319 | B2 | 6/2006 | Aliperti et al. |
| 7,135,015 | B2 | 11/2006 | Dulak et al. |
| 7,309,334 | B2 | 12/2007 | von Hoffman |
| 7,316,677 | B1 | 1/2008 | Dulak et al. |
| 7,329,268 | B2 | 2/2008 | Van Nguyen et al. |
| 7,457,661 | B2 | 11/2008 | Doty |
| 2001/0012950 | A1 * | 8/2001 | Nishtala et al. ............... 606/198 |
| 2001/0037126 | A1 | 11/2001 | Stack et al. |
| 2002/0009535 | A1 * | 1/2002 | Michal et al. .................. 427/2.1 |
| 2002/0010440 | A1 | 1/2002 | Segesser |
| 2002/0010476 | A1 | 1/2002 | Mulholland et al. |
| 2002/0077653 | A1 * | 6/2002 | Hudson et al. ................. 606/192 |
| 2002/0099431 | A1 * | 7/2002 | Armstrong et al. .......... 623/1.11 |
| 2002/0161377 | A1 | 10/2002 | Rabkin |
| 2003/0050600 | A1 | 3/2003 | Ressemann et al. |
| 2003/0065353 | A1 | 4/2003 | Horzewski et al. |
| 2003/0135156 | A1 | 7/2003 | Bencini et al. |
| 2003/0195551 | A1 | 10/2003 | Davison et al. |
| 2003/0212384 | A1 | 11/2003 | Hayeden |
| 2003/0216770 | A1 | 11/2003 | Persidsky et al. |
| 2004/0006344 | A1 * | 1/2004 | Nguyen et al. .................... 606/72 |
| 2004/0073286 | A1 | 4/2004 | Armstrong et al. |
| 2004/0087968 | A1 | 5/2004 | Core |
| 2004/0181273 | A1 | 9/2004 | Brasington et al. |
| 2004/0220549 | A1 | 11/2004 | Dittman et al. |
| 2004/0236346 | A1 | 11/2004 | Parker |
| 2005/0043780 | A1 | 2/2005 | Gifford et al. |
| 2005/0085842 | A1 * | 4/2005 | Eversull et al. ............... 606/191 |
| 2005/0124937 | A1 | 6/2005 | Kick et al. |
| 2005/0149105 | A1 | 7/2005 | Leeflang et al. |
| 2005/0222576 | A1 * | 10/2005 | Kick et al. ..................... 606/104 |
| 2006/0036276 | A1 | 2/2006 | Nguyen et al. |
| 2006/0052750 | A1 | 3/2006 | Lenker et al. |
| 2006/0142795 | A1 | 6/2006 | Nguyen et al. |
| 2006/0247602 | A1 | 11/2006 | Dulak et al. |
| 2007/0112335 | A1 | 5/2007 | Dulak et al. |

FOREIGN PATENT DOCUMENTS

| | | | | |
|---|---|---|---|---|
| EP | 0 249 45611 | | 12/1987 | |
| EP | 0385920 | | 9/1990 | |
| EP | 0 206 553 | | 1/1991 | |
| EP | 0 206 653 | | 1/1991 | |
| EP | 0206553 | * | 1/1991 | ..................... 604/264 |
| EP | 0206553 | * | 2/1991 | ............. A61B 17/34 |
| EP | 0 421 650 | | 4/1991 | |
| EP | 0 546 766 | | 6/1993 | |
| WO | 92/19312 | | 11/1992 | |
| WO | 95/30374 | | 11/1995 | |
| WO | WO 99/16499 A1 | | 4/1999 | |
| WO | WO99/16499 A1 | | 4/1999 | |
| WO | WO/99/17665 | | 4/1999 | |
| WO | 03/090834 A2 | * | 11/2003 | ..................... 604/264 |
| WO | WO 03/090834 A2 | * | 11/2003 | ............. A61M 25/06 |

OTHER PUBLICATIONS

International Preliminary Report on Patentability issued Jun. 7, 2006 for International Application No. PCT/US2004/040651 filed Dec. 3, 2004.
U.S. Pat. No. 2005/0125021 A1 (U.S. Appl. No. 10/884,017, our reference: including its prosecution history, Jun. 9, 2005, Edward J. Nance et al.
U.S. Pat. No. 2006/0200188 A1 (U.S. Appl. No. 11/415,659, our reference: including its prosecution history, the Office Action mailed Jan. 10, 2007, the Amendment filed Jun. 11, 2007, Sep. 7, 2006, Edward J. Nance et al.
U.S. Pat. No. 2006/0200189 A1 (U.S. Appl. No. 11/415,764, our reference: including its prosecution history, the Office Action mailed Jan. 8, 2007, the Amendment filed Jun. 8, 2007, Sep. 7, 2006, Edward J. Nance et al.
Feb. 5, 2009 Restriction Requirement in U.S. Appl. No. 11/884,017, filed Jul. 2, 2004.
Mar. 2, 2009 Response to Feb. 5, 2009 Restriction Requirement in U.S. Appl. No. 11/884,017, filed Jul. 2, 2004.
Apr. 17, 2009 Non-final Rejection in U.S. Appl. No. 11/884,017, filed Jul. 2, 2004.
Jan. 10, 2007 Non-final Rejection in U.S. Appl. No. 11/415,659, filed May 2, 2006.
Jun. 11, 2007 Response to Jan. 10, 2007 Non-final Rejection in U.S. Appl. No. 11/415,659, filed May 5, 2006.
Aug. 20, 2007 Final Rejection in U.S. Appl. No. 11/415,659, filed May 2, 2006.
Nov. 7, 2007 Response to Aug. 20, 2007 Final Rejection in U.S. Appl. No. 11/415,659, filed May 2, 2006.
Nov. 16, 2007 Advisory Action in U.S. Appl. No. 11/415,659, filed May 2, 2006.
Feb. 20, 2008 Response to Aug. 20, 2007 Final Rejection in U.S. Appl. No. 11/415,659, filed May 2, 2006.
May 20, 2008 Non-final Rejection in U.S. Appl. No. 11/415,659, filed May 2, 2006.
Nov. 19, 2008 Response to May 20, 2008 Non-final Rejection in U.S. Appl. No. 11/415,659, filed May 2, 2006.
Apr. 6, 2009 Final Rejection in U.S. Appl. No. 11/415,659, filed May 2, 2006.
May 11, 2009 Response to Apr. 6, 2009 Final Rejection in U.S. Appl. No. 11/415,659, filed May 2, 2006.
Jan. 8, 2007 Non-final Rejection in U.S. Appl. No. 11/415,764, filed May 2, 2006.
Jun. 8, 2007 Response to Jan. 8, 2007 Non-final Rejection in U.S. Appl. No. 11/415,764, filed May 2, 2006.
Aug. 20, 2007 Non-final Rejection in U.S. Appl. No. 11/415,764, filed May 2, 2006.
Feb. 20, 2008 Response to Aug. 20, 2007 Non-final Rejection in U.S. Appl. No. 11/415,764, filed May 2, 2006.
Jun. 13, 2008 Non-final Rejection in U.S. Appl. No. 11/415,764, filed May 2, 2006.
Dec. 12, 2008 Response to Jun. 13, 2008 Non-final Rejection in U.S. Appl. No. 11/415,764, filed May 2, 2006.
Oct. 3, 2008 Non-final Rejection in U.S. Appl. No. 11/223,897, filed Sep. 9, 2005.
Feb. 3, 2009 Response to Oct. 3, 2008 Non-final Rejection in U.S. Appl. No. 11/223,897, filed Sep. 9, 2005.
Apr. 17, 2009 Final Rejection in U.S. Appl. No. 11/223,897, filed Sep. 9, 2005.
May 12, 2009 Response to Apr. 17, 2009 Final Rejection in U.S. Appl. No. 11/223,897, filed Sep. 9, 2005.
Jan. 30, 2008 European Patent Office Communication in Euro. App. No. 04813043.9 filed Mar. 12, 2004.
Aug. 11, 2008 Response to Jan. 30, 2008 European Patent Office Communication in Euro. App. No. 04813043.9 filed Mar. 12, 2004.
May 25, 2009 European Patent Office Communication in Euro. App. No. 04813043.9 filed Mar. 12, 2004.
Oct. 16, 2009 Response to Apr. 17, 2009 Non-final Rejection in U.S. Appl. No. 11/884,017, filed Jul. 2, 2004.
Jul. 22, 2009 Non-final Rejection in U.S. Appl. No. 11/415,659, filed May 2, 2006.
Jun. 30, 2009 Final Rejection in U.S. Appl. No. 11/415,764, filed May 2, 2006.
Jun. 30, 2009 Non-final Rejection in U.S. Appl. No. 11/223,897, filed Sep. 9, 2005.
Sep. 15, 2009 Response to Jun. 30, 2009 Non-final Rejection in U.S. Appl. No. 11/223,897, filed Sep. 9, 2005.
Jan. 8, 2007 Non-final rejection in U.S. Appl. No.: 11/415,764, filed May 2, 2006.

(56) References Cited

OTHER PUBLICATIONS

Mar. 19, 2010 Non-final rejection in U.S. Appl. No. 11/415,764, filed May 2, 2006.
Jan. 15, 2009 Response to Jul. 14, 2008 European Patent Office Communication in European Application No. 05 794 899.4 filed Sep. 8, 2005.
Jan. 30, 2008 European Patent Office communication in European Application No. 04813043.9 filed Mar. 12, 2004.
Jun. 15, 2006 International Preliminary Report in International Application No. PCT/US2004/040651 filed Dec. 3, 2004.
Jul. 14, 2008 European Patent Office Communication in European Application No. 05 794 899.4 filed Sep. 8, 2005.
European Search Report Application No. 05794899.4.
International Search Report for Application No. PCT/US05/31958 mailed Apr. 3, 2007.
Apr. 15, 2011 European Patent Office Communication in European Application No. 04813043.9 filed Dec. 3, 2004.

* cited by examiner

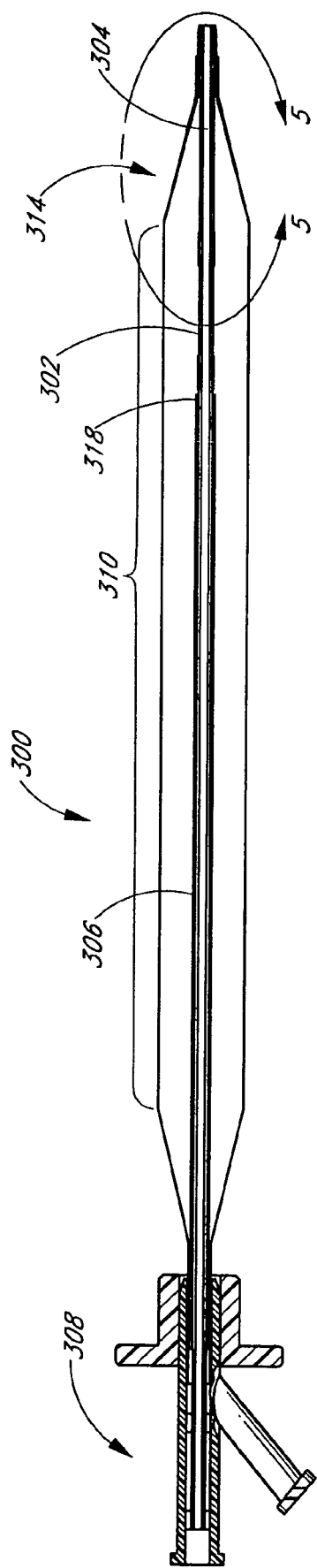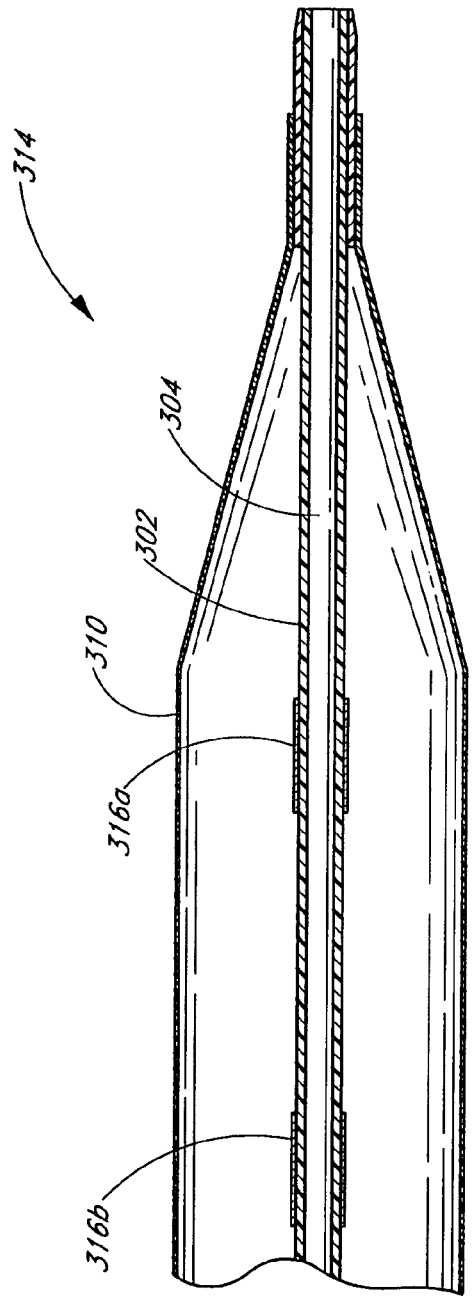
FIG. 4
FIG. 5

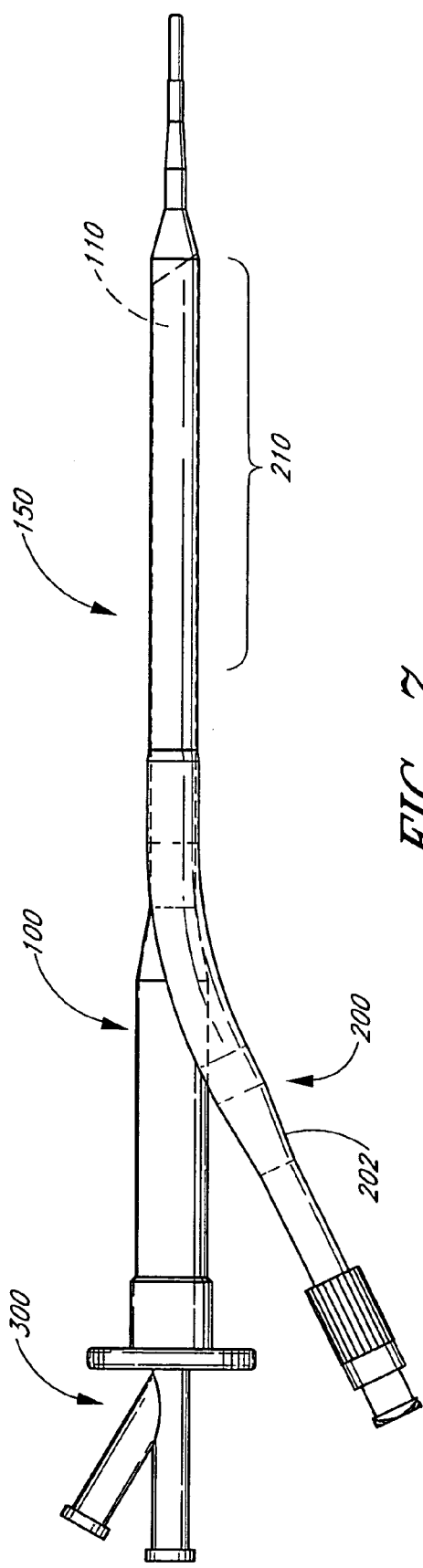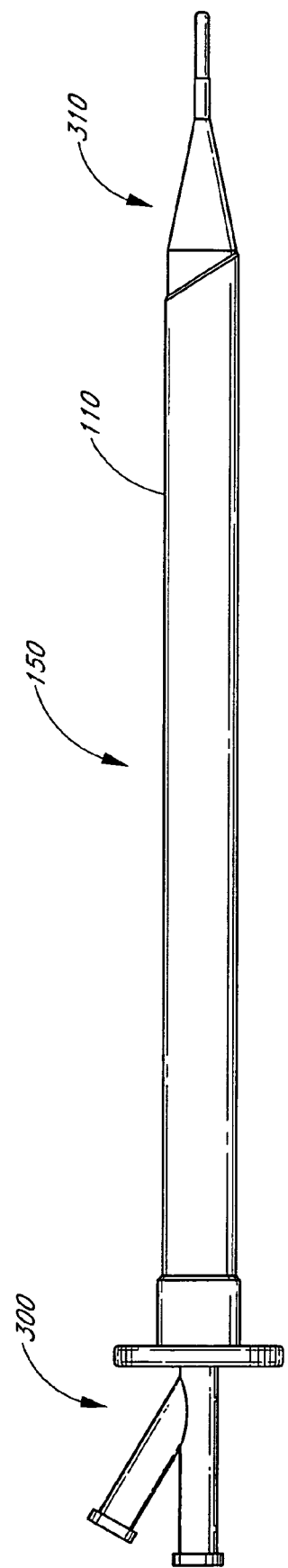
FIG. 7
FIG. 8

EXPANDABLE PERCUTANEOUS SHEATH

BACKGROUND OF THE INVENTION

1. Field of the Invention

The present invention relates to medical devices and, more particularly, to methods and devices for forming a percutaneous channel. In one application, the present invention relates to methods and devices for providing percutaneous access to a soft tissue or organ.

2. Description of the Related Art

A wide variety of diagnostic or therapeutic procedures involve the introduction of a device through a natural or artificially created access pathway. A general objective of access systems, which have been developed for this purpose, is to minimize the cross-sectional area of the puncture, while maximizing the available space for the diagnostic or therapeutic instrument. These procedures include, among others, a wide variety of laprascopic diagnostic and therapeutic interventional procedures.

Percutaneous nephrostomy is an example of one type of therapeutic interventional procedure that requires an artificially created pathway. Percutaneous nephrostomy is a minimally invasive procedure that can be used to provide percutaneous access to the upper urinary tract. At first, percutaneous nephrostomy was used only for urinary diversion but now it may be used for more complex procedures such as stone extraction, integrate endopyelotomy, and resection of transitional cell carcinoma of the upper urinary tract.

In many percutaneous nephrostomy systems, a stiff guidewire is first placed into the renal collection system through the renal parenchyma and the ureter using fluoroscopic control. A second "safety wire" may be placed with a dual lumen catheter for maintaining the tract should the first wire become dislodged or kinked.

Once guidewire control is established, a dilator sheath is used to create the tract and establish a rigid working lumen. An early technique involved advancing a flexible, 8 French, tapered catheter over the first guidewire to provide guidewire protection as well as a stable path for the placement of larger diameter dilators and sheaths. The larger diameter sheaths are sequentially advanced over the catheter and each other until an approximately 34 French tract is established. The inner sheaths or dilators may then be sequentially removed such that the outermost sheath defines a working lumen. In this system, tract formation is accomplished by the angular shearing force of each subsequent sheath placement, which cuts a path through the tissue. Because axial pressure is required to advance and place each sheath, care must be taken to avoid kinking the tapered catheter and/or advancing the sheaths to far and perforating the renal pelvis. This technique also requires a large number of steps.

A more recent technique utilizes a balloon that is advanced over the first guide wire. Once in place in the renal pelvis, the balloon is inflated with a dilute contrast media solution to enlarge the tract. Once the balloon is inflated to a suitable diameter, a rigid sheath is advanced over the balloon. Advancing the rigid sheath over the balloon typically requires applying axial force to the sheath and rotation. The balloon may then be deflated and removed from the rigid sheath so that the rigid sheath may define a working lumen. In general, this technique is considered less traumatic than the previously described technique. Nevertheless, placement of the rigid sheath still involves angular shearing forces and several steps.

Additional information regarding percutaneous nephrostomy can be found in McDougall, E. M., et al. (2002), Percutaneous Approaches to the Upper Urinary Tract, *Campbell's Urology*, 8th ed, vol. 4, pp. 3320-3357, Chapter 98. Philadelphia, Saunders.

A need therefore remains for improved access technology which allows a device to be percutaneously passed through a small diameter tissue tract, while accommodating the introduction of relatively large diameter instruments.

SUMMARY OF THE INVENTION

A percutaneous access sheath is provided according to an embodiment of the present invention. In one application, the percutaneous access sheath is used to provide access to the upper urinary tract or bladder.

In one embodiment, the percutaneous access sheath may be used in conjunction with a deployment catheter, which may be provided with a balloon at its distal end. The percutaneous access sheath has a proximal section and a variable diameter distal section. The deployment catheter may be disposed within the percutaneous access sheath such that the balloon is positioned within the distal section of the percutaneous access sheath.

In one embodiment, the distal section of the percutaneous access sheath is restrained in a first, small diameter by a releasable restraint such as a perforated, scored or thin wall continuos film insert jacket. The distal section of the percutaneous access sheath is creased by at least 2 to 4 or 2 to 6 folds and inserted into a distal section of the jacket. This gives the percutaneous access sheath a smaller cross-sectional profile, facilitating its insertion.

In one embodiment, the folded percutaneous access sheath is restrained within the jacket. Following insertion into a patient's anatomy, the jacket may be released by inflating the balloon on the deployment catheter. During the inflation process, the jacket separates along its longitudinal axis as the access sheath unfolds and/or expands. In one preferred embodiment, separation of the jacket during inflation, occurs along a perforated or scored line formed on the jacket. In one such embodiment, the score or perforation may be formed at or close to the distal end of the jacket such that the jacket separates at the distal end first. In another preferred embodiment, the jacket is formed from a continuous film and the separation is caused by stretching the film until it separates. After the balloon has expanded the access sheath to its full diameter and caused the jacket to separate, the jacket may be withdrawn from the patient's anatomy. In a modified embodiment, the jacket may remain coupled to the access sheath during use. The balloon may be deflated to allow the removal of the deployment catheter, leaving the percutaneous access sheath in place.

In one embodiment where the percutaneous access sheath is used to provide access to the upper urinary tract, the percutaneous access sheath may be used to provide access by tools adapted to perform biopsy, urinary diversion, stone extraction, antegrade endopyelotomy, and resection of transitional cell carcinoma and other diagnostic or therapeutic procedures of the upper urinary tract or bladder Other applications of the percutaneous access sheath include a variety of diagnostic or therapeutic clinical situations which require access to the inside of the body, through either an artificially created or natural body lumen.

BRIEF DESCRIPTION OF THE DRAWINGS

FIG. 4 is a side elevational view of an access sheath expansion balloon catheter.

FIG. 5 is an enlarged view of the distal end of the expansion balloon catheter.

FIG. 7 illustrates the percutaneous access sheath assembly, with the expansion balloon catheter inserted into the structure illustrated in FIG. 3.

FIG. 8 illustrates the percutaneous access sheath assembly of FIG. 7 in an expanded configuration and the jacket removed.

DETAILED DESCRIPTION OF THE PREFERRED EMBODIMENT

Figure 1:
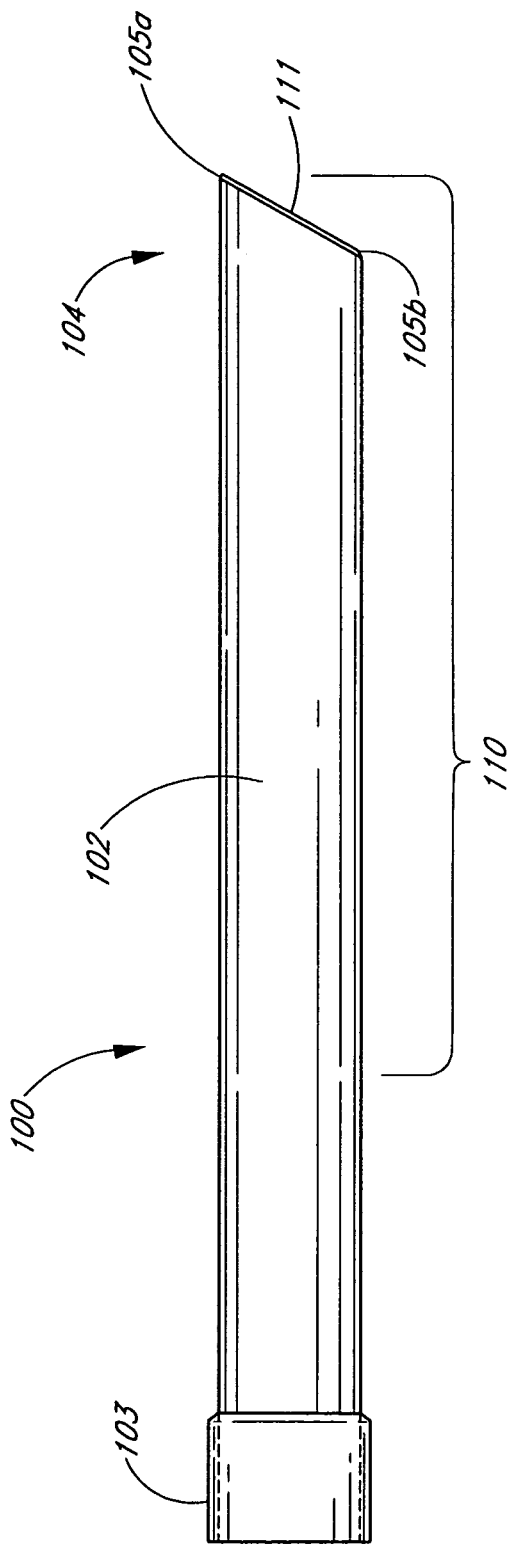
FIG. 1 is a side elevational view of a percutaneous access sheath.
Figure 1A:
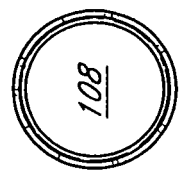
FIG. 1A is a front view of the percutaneous access sheath.

FIG. 1 is an overview of an exemplary embodiment of a percutaneous access sheath 100. The sheath 100 generally comprises an elongate tubular body 102 with an axial lumen 108 (FIG. 1A), and is designed to provide percutaneous access to a diagnostic or treatment site in the body.

In the exemplary embodiment, the elongate tubular body 102 has a distal section 110 and a proximal section 103. The proximal section 103 has a slightly larger inner and outer diameter as compared to the distal section 110. As will be explained in more detail below, the proximal section 103 may be used to secure the access sheath 100 to a connector. With continued reference to FIG. 1, the distal end 104 of the distal section 110 may be provided with a beveled distal face 111, which preferably forms an angle of about 45 to about 75 degrees with respect a longitudinal axis of the tubular body 102. In this manner, the distal face 111 forms a leading edge 105a and a trailing edge 105b. As will be explained below, during insertion, the beveled face 111 advantageously provides the distal end 104 of the access sheath 100 with a smaller cross-sectional profile in a compressed configuration. This provides a smoother transition from the distal end 104 of the access sheath 100 to the deployment catheter (described below). In addition, in the expanded configuration, the leading edge 105a maintains positional purchase within the target tissue or organ while the trailing edge 105b provides the sheath 100 with an aperture to facilitate instrument maneuvering and visualization within the internal structure of the tissue or organ under examination or treatment. In a modified embodiment, the distal face 111 may be form an angle of about 90 degrees with respect to the longitudinal axis of the tubular body.

The length and diameter of the sheath 100 can be varied according to clinical need, as will be understood by those skilled in the art with reference to this disclosure. In one exemplary embodiment for percutaneous nephrostomy, the access sheath 100 has an overall length of about 17 to about 30 centimeters with the distal section 110 having a length of about 11 to about 24 centimeters. As will be explained in more detail below, a portion or all of the distal section 110 is expandable from a first, smaller cross-sectional profile to a second, larger cross-sectional profile. The first, smaller cross-sectional profile of the distal section 110 eases its insertion into a percutaneous treatment site. After insertion, the distal section 110 is expanded to a second, larger cross-sectional profile to provide a larger passageway for surgical instruments to reach the percutaneous treatment site. For percutaneous nephrostomy, the smaller cross-sectional profile may have a diameter of about 15 French to about 24 French and the larger cross-sectional profile may have a diameter of about 21 French to about 40 French. In the larger cross-sectional profile, the lumen 108 may have a diameter of about 18 French to about 38 French.

As mentioned above, in the illustrated embodiment, the percutaneous access sheath 100 comprises a tubing 102, which defines a lumen 108. The tubing 102 may be made of PTFE, nylon, PEBAX or polyethylene, polyurethane, silicone, or other suitable materials.

In this embodiment, the distal section 110 is creased in at least two and more preferably 2 to 6 sections, most preferably 2 to 4 sections, and collapsed from a larger to a smaller cross-sectional profile to ease its insertion. As discussed below, in one embodiment for percutaneous nephrostomy, the distal section 110 is placed into the renal collecting system through the renal parenchyma and ureters. Its length is thus determined by the anatomy and is generally in the range of about 11 cm to about 24 cm. In the illustrated embodiment, the proximal end 103 of the tubing 102 is flared and fitted onto the deployment catheter as will be explained below. The overall length of the tubing 102 depends on the distance between the insertion and treatment locations, and is generally in the range of 10-100 cm for various clinical indications. As mentioned above, for percutaneous nephrostomy, the length of the tubing is approximately 17-30 cm.

Figure 2:
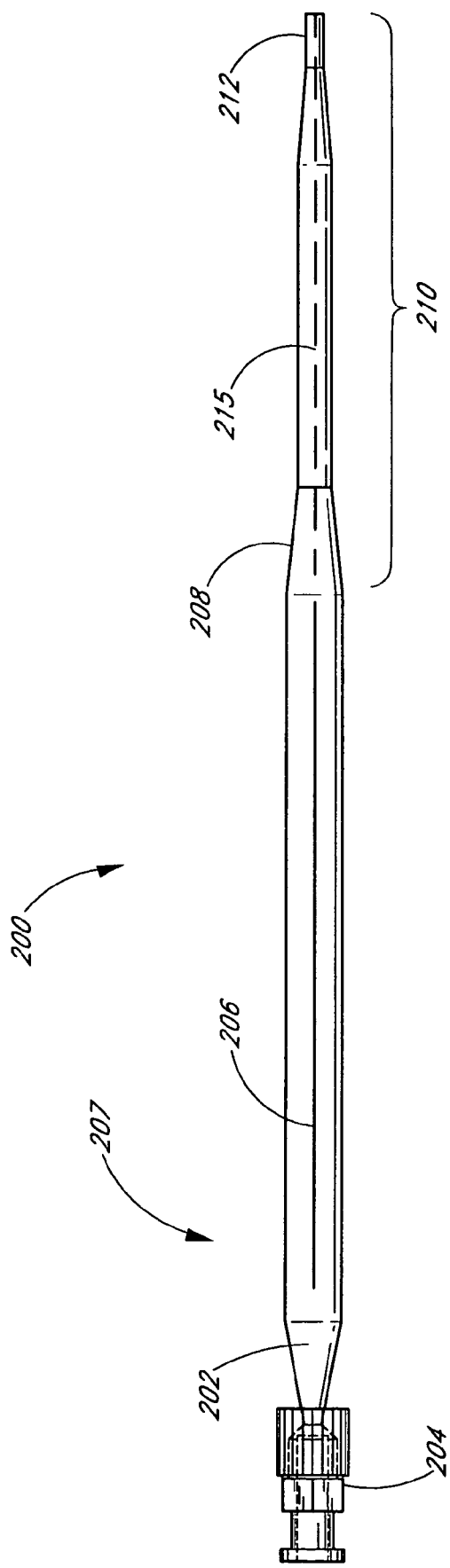
FIG. 2 is a side elevational view of a jacket.

FIG. 2 is an overview of the jacket 200. It is preferably made of a thin, smooth and flexible material. The jacket 200 has a proximal section 207 and a distal, restraint section 210. The restraint section 210 has a smaller cross-sectional profile than the proximal section 207 of the jacket 200. The restraint section 210 is adapted to restrain a portion or all of the distal section 110 of the percutaneous access sheath 100 in a smaller cross-sectional profile. This is achieved by constraining the percutaneous access sheath 100 in the jacket 200 such that all or a portion of the distal section 110 of the percutaneous access sheath 100 lies within the restraint section 210 of the jacket 200.

In the illustrated embodiment, the jacket 200 may be made of heat shrink PTFE. The proximal end 202 of the jacket 200 terminates at a pull tab 204, which may be formed by any of a variety of structures such as a threaded connector with a luer lock at its proximal end. The jacket 200 may be provided with a slit 206 near its proximal end 202. The jacket 200 tapers at a first tapering point 208 into a restraint section 210, which tapers again into the distal tip 212. As discussed above, the restraint section 210 restrains the distal section 110 of the percutaneous access sheath 100 in its smaller cross-sectional profile. Thus the length of the restraint section 210 is approximately the same as or slightly longer or shorter than the distal section 110, and generally falls in the range of about 11-25 cm.

The outside diameter of the restraint section 210 is preferably configured to ease its insertion into a percutaneous treatment site. Depending upon the clinical application, the outside diameter may be in the range of about 3 French to about 40 French. For percutaneous nephrostomy, the outside diameter may be in the range of about 5 French to about 35 French. The restraint section 210 is configured to separate and/or tear preferably along its longitudinal axis to release the access sheath 100 as it is radially expanded. In the illustrated embodiment, the jacket 200 is perforated, scored or otherwise provided with a tear line 215 from the first tapering point 208 to its distal tip 212. In another embodiment, the jacket 200 may be constructed of a material that will disrupt or separate during expansion from the first tapering point 208 to its distal tip 212. In another embodiment, the jacket 200 may be perforated, scored or otherwise provided with a tear line for only a portion of the restraint section 210. For example, in one embodiment, the restraint section 210 may be provided with a tear line at a region close to or at the distal end of the jacket 200. This may cause the jacket 200 to disrupt or separate during expansion from its distal end first The distance between the slit 206 and the distal tip 212 is generally approximately equal to or longer than the length of the folded, compressed portion of the tubing 102 such that the folded compressed portion of the tubing 102 terminates within the restraint section 210. In one embodiment, this arrangement permits complete disruption of the jacket 200 when the access sheath 100 is fully expanded. In one embodiment, the distance between the slit 206 and the distal tip 212 is generally in the range of 6-90 cm for most clinical applications and about 11-24 cm for percutaneous nephrostomy. In the illustrated embodiment, which is configured for percutaneous nephrostomy, this distance is approximately 11 cm, and the overall length of the jacket 200 is approximately 19 cm.

Figure 3:
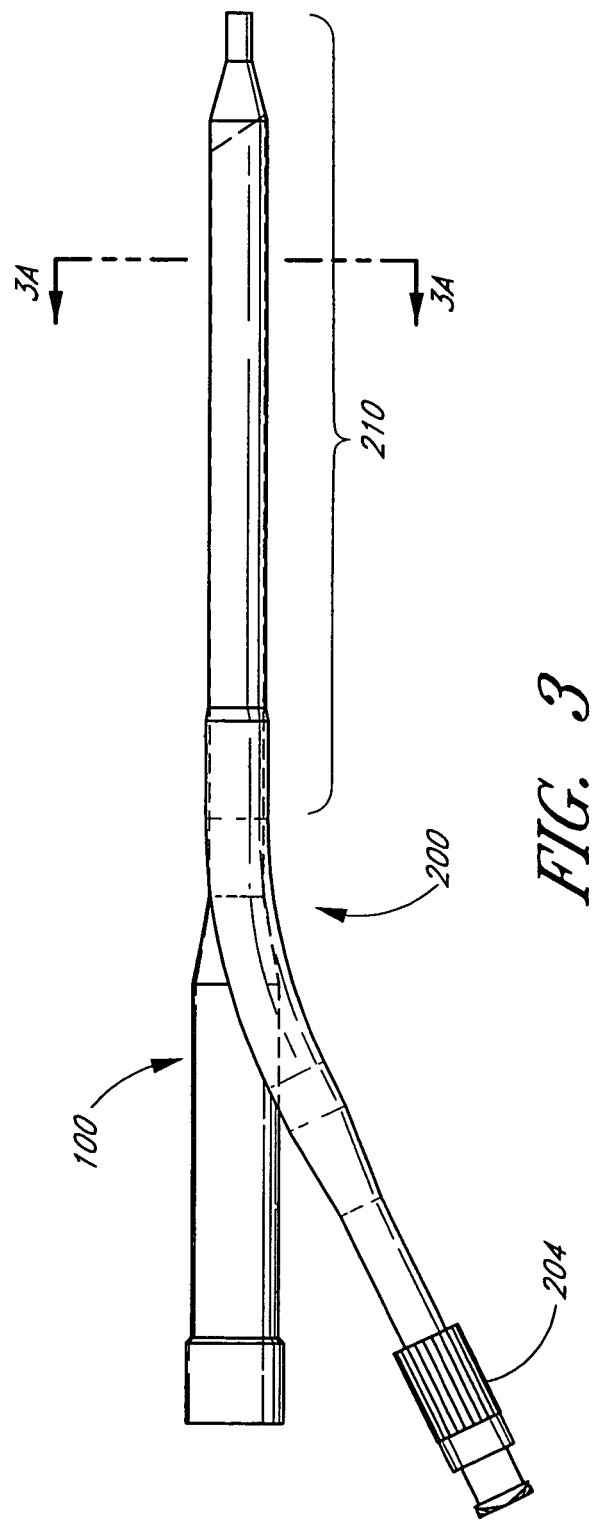
FIG. 3 illustrates the percutaneous access sheath in a reduced cross-sectional configuration and inserted into the jacket.

FIG. 3 illustrates the percutaneous access sheath 100 inserted into the jacket 200 via the slit 206 provided near its proximal end 202. The diameter of the restraint section 210 of the jacket 200 is smaller than the diameter of the distal section 110 of the tubing 102. In the illustrated embodiment, the distal section 110 is creased and folded inwards to decrease its effective diameter, and inserted into the restraint section 210. As discussed above, the restraint section 210 restrains the distal section 110 of the percutaneous access sheath 100 in its smaller cross-sectional profile. The restraint section 210 may be approximately the same length as or shorter than the distal section 110. In the illustrated embodiment, the restraint section 210 is approximately 11-24 cm.

As will be explained in more detail below, in some embodiments, the jacket 200 is removed from the access sheath 100 and the surgical site after the sheath 100 is expanded. In other embodiments, the jacket 200 is attached to the sheath 100 and remains attached to the sheath 100 after it is expanded and during the surgical procedure. In such latter embodiments, the jacket 200 may be securely attached to the access sheath by, for example, at least one adhesive or heat bond, preferably extending axially along a section of the access sheath 100 generally opposite the folds or creases.

In certain embodiments a jacket 200 may not be necessary if the distal section 110 of the percutaneous access sheath 100 is made of a stretchable material that may be stretched from a first, smaller cross-sectional profile to a second, larger cross-sectional profile. In these embodiments the outer surface of the distal section 110 is preferably made of a smooth material to facilitate the insertion of the percutaneous access sheath 100 into a treatment site. In still other embodiments, the jacket 200 may be a stretchable material that may be stretched with or without elastic deformation from a first, smaller cross-sectional profile to a second, larger cross-sectional profile as the sheath is expanded.

FIG. 4 is an overview of the deployment catheter 300. It is provided with an expansion element such as balloon 310. As will be explained in more detail below, the deployment catheter 300 is inserted into the lumen 108 of the percutaneous access sheath 100 such that the balloon 310 is arranged within the distal section 110. The balloon 310 may then be inflated to expand the distal section 110 from its first, smaller cross-sectional profile to its second, larger cross-sectional profile following the insertion of the percutaneous access sheath 100 into a treatment site.

With particular reference to FIG. 4, an inner tube 302 extends the entire length of the deployment catheter 300. A guide wire lumen 304 is defined by the interior of the inner tube 302. The deployment catheter 300 can travel along a guide wire extending through the guide wire lumen 304. The inner tube 302 carries coaxially on its exterior an outer tube 306. The outer tube 306 terminates proximally into the distal end of a y-connector 308, and distally into a balloon 310. The balloon 310 may be made of PET. The y-connector 308 may be provided with an optional support tube (not shown) extending from its distal end and over a proximal section of the outer tube 306, to increase the rigidity of the deployment catheter 300 during insertion. This support tube may be made of any of a variety of materials, such as, a stainless steel hypotube.

FIG. 5 is an enlarged view of the distal end 314 of the exemplary embodiment of the deployment catheter 300. Both the inner tube 302 and the guide wire lumen 304 extend through the distal end 314 of the balloon 310. The inner tube 302 may carry coaxially on its exterior a pair of marker rings 316a, 316b near the distal end 314 of the balloon 310. With reference to FIG. 8, the pair of markers 316a, 316b are spaced apart such that when the deployment catheter 300 is inserted into the lumen 108 and expanded they correspond to the distal edge 105a and proximal edge 105b of the beveled distal face 111 (see FIG. 1). In a modified arrangement, the markers 316a, 316b may be carried by the distal end 314 of the balloon 310. The markers 316a,b ma be made of gold, tantalum, platinum or another radio-opaque material. Additional markers may be provided on the deployment catheter to aid in visualizing its location. In another embodiment, the markers 316a, 316b may be replaced with a single axially elongated marker having a leading and trailing edge that corresponds to the distal edge 105a and proximal edge 105b of the beveled distal face 111.

With reference back to FIGS. 4, a balloon inflation lumen 318, defined in the space between the inner tube 302 and the outer tube 306, communicates with the interior of the balloon 310. As discussed above, the balloon 310 may be inflated to expand the distal section 110 of the percutaneous access sheath 100 from its first, smaller cross-sectional profile to its second, larger cross-sectional profile. Thus the length of the balloon 310 is approximately equal to or slightly longer than the length of the distal section 110. In the illustrated embodiment, which is configured for percutaneous nephrostomy the length of the balloon 310 is approximately 12.5 cm. For other clinical applications, the length of the balloon 310 may be in the range of about 8-90 cm.

Figure 6:
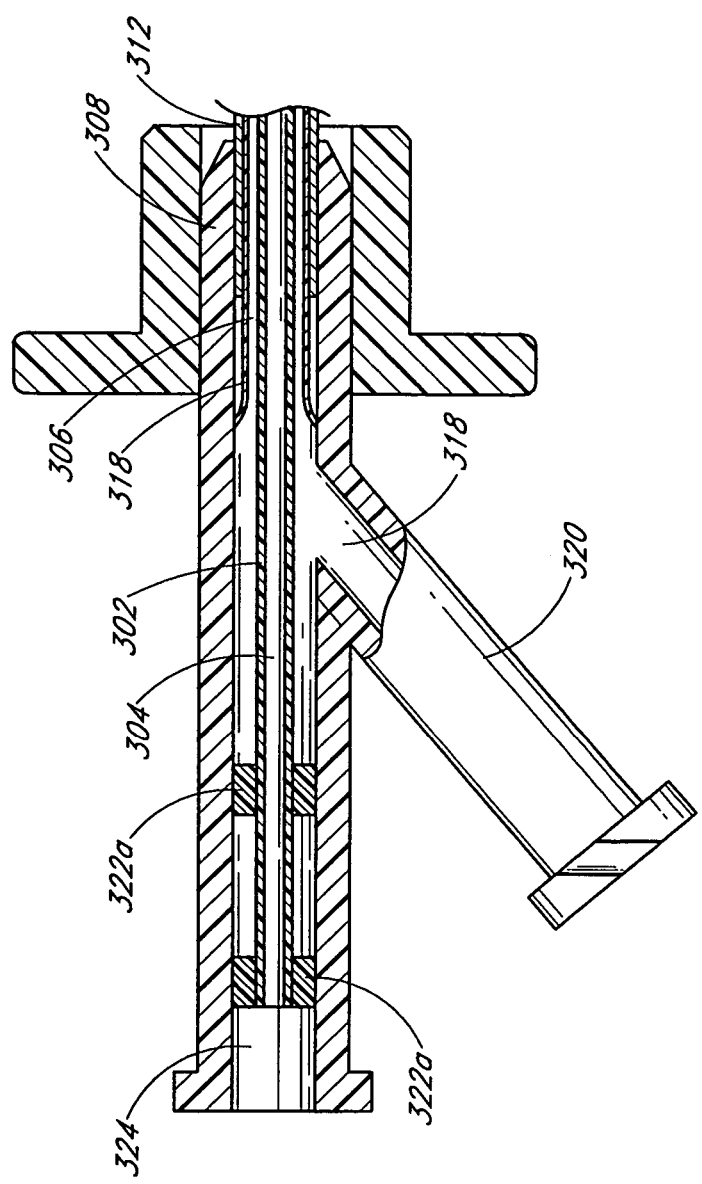
FIG. 6 is an enlarged view of the proximal end of the expansion balloon catheter.

FIG. 6 is an enlarged view of the proximal end of the illustrated embodiment of the deployment catheter 300. Both the inner tube 302 and the guide wire lumen 304 extend through the distal end of the y-connector 308. The balloon inflation lumen 318, defined in the space between the inner tube 302 and the outer tube 306, opens into a port 320 in the y-connector 308. The illustrated embodiment uses a pair of stoppers 322a, 322b to align the inner tube 302 within the y-connector 308 and prevent the balloon inflation lumen 318 from communicating with the space 324 in the main branch of the y-connector 308. Thus only the port 320 communicates via the balloon inflation lumen 318 with the interior of the balloon. A pump may be connected to the port 320 to inflate or deflate the balloon. To enable visualization of the state of the balloon, it may be inflated with contrast media.

FIG. 7 illustrates the percutaneous access sheath assembly 150 in a collapsed or smaller profile configuration. The percutaneous access sheath assembly 150 comprises the percutaneous access sheath 100, the jacket 200 and the deployment catheter 300. It is assembled by inserting the deployment catheter 300 into the percutaneous access sheath 100 and inserting the percutaneous access sheath 100 into the jacket 200 such as via the slit 206 or other proximal opening provided near its proximal end 202. The balloon 310, which is not shown in FIG. 7, of the deployment catheter 300 is deflated, folded and inserted into the distal section 110 of the access sheath 100. The distal section 110, as discussed above, is creased and folded inwards to decrease its effective diameter, and inserted into the restraint section 210 of the jacket 200. As discussed, the balloon 310 is approximately the same length as or just longer than the distal section 110 and the restraint section 210.

FIG. 8 illustrates the percutaneous access sheath assembly 150 in an expanded or larger profile configuration. In the expanded configuration, the jacket 200 has been removed and the balloon 310 has been inflated to expand the distal section 110 of the access sheath 100.

Figure 9:
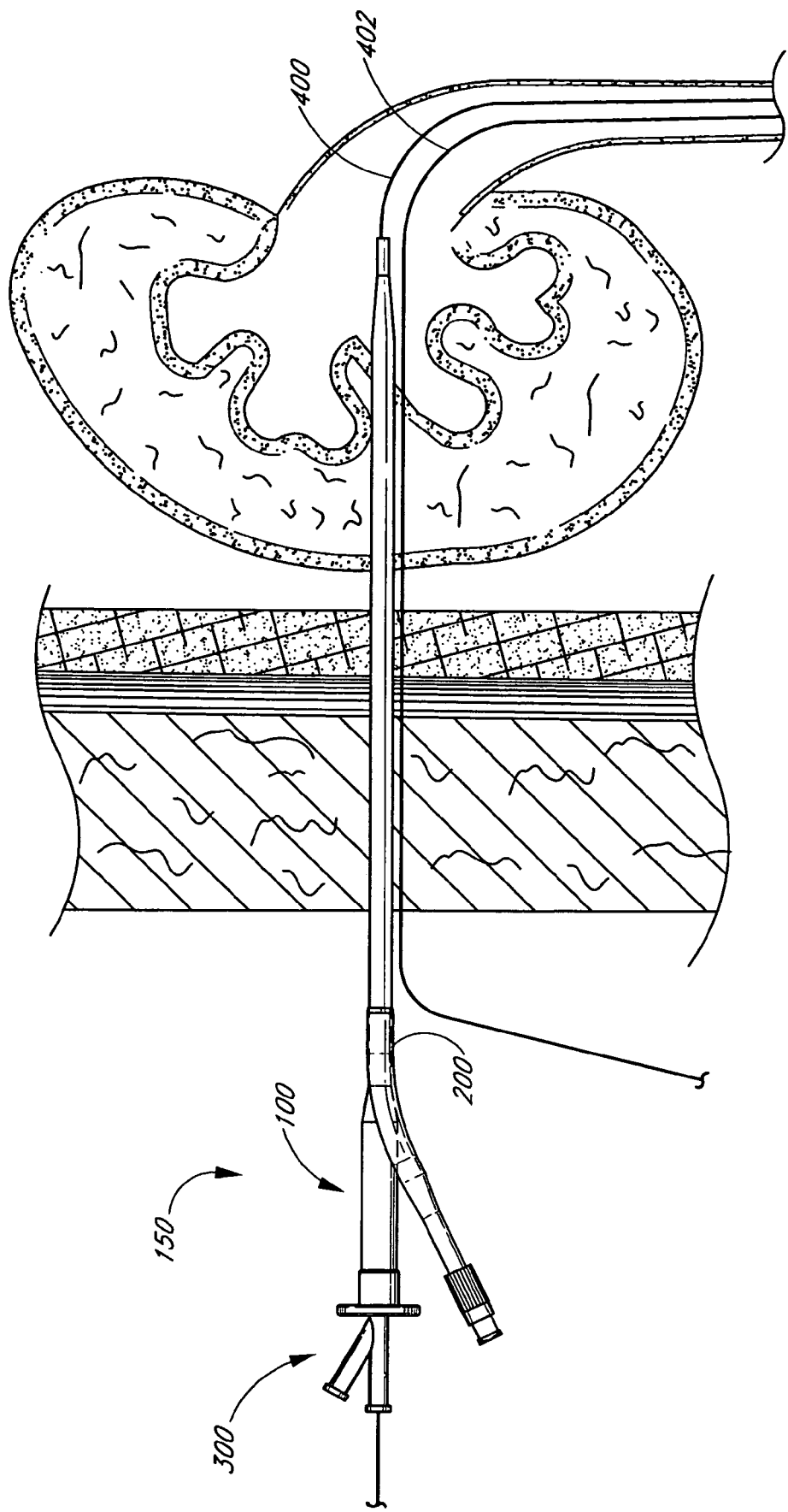
FIG. 9 illustrates the percutaneous access sheath assembly of FIG. 7 inserted into a renal calyx of a kidney, in a first, low profile configuration.
Figure 10:
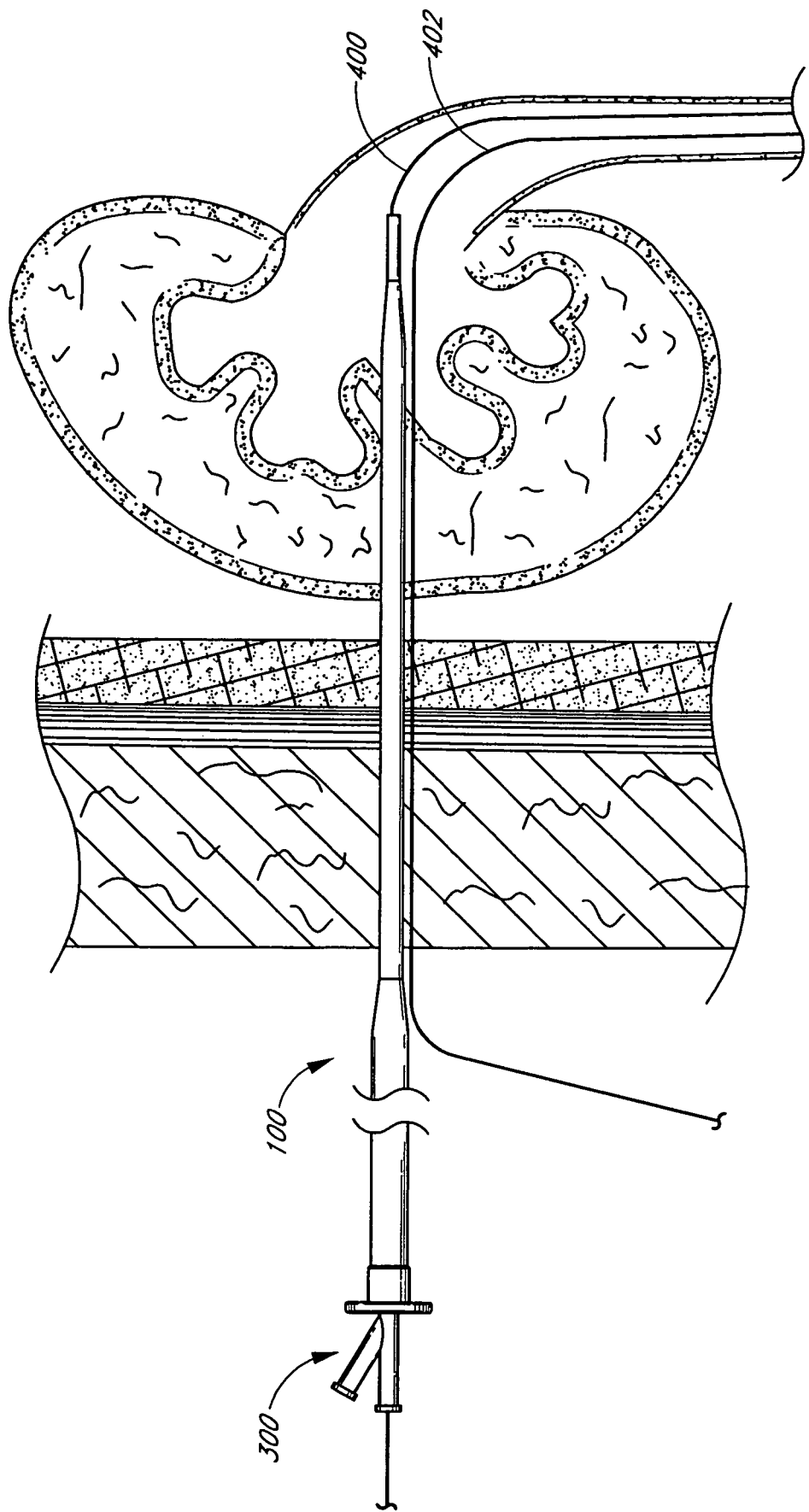
FIG. 10 illustrates the percutaneous access sheath assembly of FIG. 9 with the jacket removed.
Figure 11:
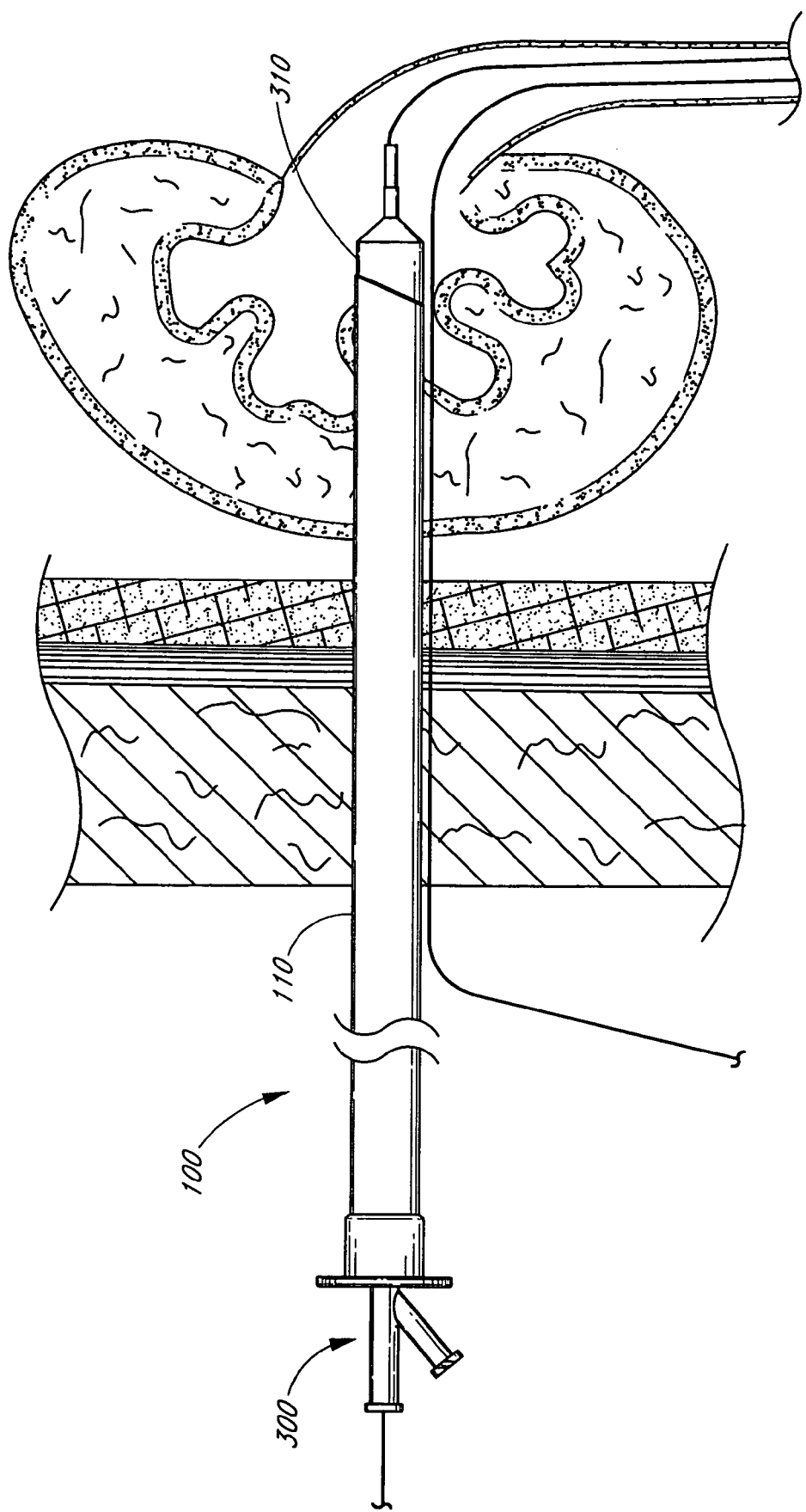
FIG. 11 illustrates the percutaneous access sheath assembly of FIG. 10 with the jacket removed and the expansion catheter fully expanded in a second, functional configuration.
Figure 12:
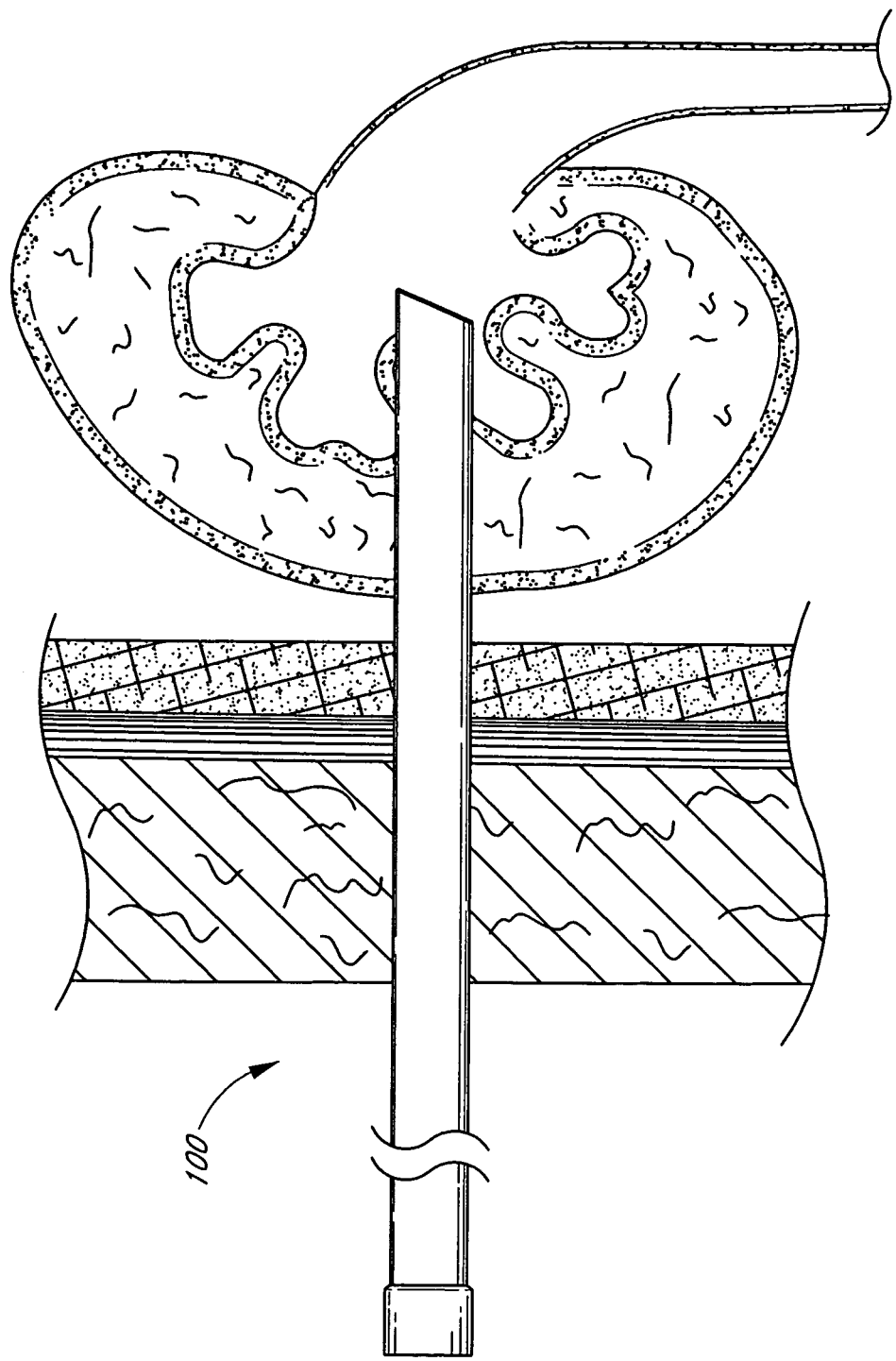
FIG. 12 illustrates the percutaneous access assembly of FIG. 11 with the expansion catheter removed.

One exemplary embodiment of use will now be described with reference to FIGS. 9-12. As shown in FIG. 9, a guidewire 400 may be placed into the renal collection system. In one embodiment, the guidewire 400 is inserted through the renal parenchyma and the ureter using fluoroscopic control. The guidewire 400 may be 0.038" stiff guidewire that is inserted through a small (e.g., 1.7 to two centimeter) incision made at the guidewire skin entry cite. A second "safety wire" 402 may be placed with a dual lumen catheter (not shown) for maintaining the tract should the first wire become dislodged or kinked.

The guide wire 400 may be inserted into the guide wire lumen 304 (see FIG. 4) of the deployment catheter 300 of the percutaneous access sheath assembly 150. The entire assembly 150 may travel over the guide wire 400 until its distal tapered portion is positioned just within the renal pelvis. As mentioned above, the distal tip 314 is preferably provided with a pair of radiopaque tip markers 316a, 316b to aid placement. The jacket 200, which is on the exterior of the percutaneous access sheath assembly 150, facilitates the insertion because of its smooth, low profile exterior.

Following the insertion of the percutaneous access sheath assembly 150, the access sheath 100 may be expanded and released from the jacket 200. This may be accomplished by inflating, at least partially, the balloon 310 (not visible in FIG. 10) and radially expanding the access sheath 100 until the jacket 200 separates, preferably along the longitudinal axis of the jacket 200. As discussed above, the balloon 310 is arranged within the distal section 110 of the percutaneous access sheath 100, which is itself arranged within the restraint section 210 of the jacket 200. Thus, inflating the balloon 310 causes the distal section 110 of the percutaneous access sheath 100 to expand, tearing or separating the restraint section 210 of the jacket 200 preferably along its longitudinal axis.

After the sheath 100 is released from the jacket 200, the balloon 310 may be fully inflated to expand the distal section 110 of the percutaneous access sheath to its full cross-sectional profile. See FIG. 11. In one embodiment, the balloon 310 is inflated by providing a pump (e.g., a high pressure balloon inflation syringe) with about 20-25 cc of a diluted contrast media (e.g., a 50% solution of Renografin® and sterile saline). After removing the air from the pump and associated tubing, the pump may be attached to the inflation/deflation port of the central balloon shaft. Preferably, under fluoroscopic control, the dilute contrast media is slowly injected until a maximum pressure of about 12 bar is achieved. Inflation pressure is preferably maintained for a minimum of about 60 seconds to reduce or eliminate any "waist" (i.e., partially unexpanded sections) that may remain along the length of the expanded sheath 100.

In some embodiments, after the sheath 100 has been released from the jacket 200, the jacket 200 may be removed from the access sheath 100 and the surgical cite. In other embodiments, the jacket 200 may remain attached to the access sheath 100 during use. As explained above, in such embodiments, the jacket 200 may be securely attached to the access sheath by, for example, an adhesive or heat bond.

After the balloon 310 is inflated, it may be deflated to ease the removal of the deployment catheter 300. As discussed above, the inflation and deflation of the balloon 310 may be done via a pump connected to the port 320 of the deployment catheter 300, and preferably with a dilute contrast media being pumped, to better convey the state of the balloon.

Thus, the percutaneous access sheath 100 extends into the renal pelvis and provides a working lumen. See FIG. 12. The establishment of this working lumen may provide access for several procedures such as biopsy, stone extraction, antegrade endopyelotomy, and resection of transitional cell carcinoma of the upper urinary tract. As explained above, in the embodiments with a beveled edge 111, the leading edge 105a maintains positional purchase within the target tissue or organ while the trailing edge 105b provides the sheath 100 with an aperture to facilitate instrument maneuvering and visualization within the internal structure of the tissue or organ under examination or repair.

It will be apparent from the disclosure herein that the percutaneous access sheath 100, the percutaneous access sheath assembly 150, and/or the methods described herein may also find utility in a wide variety of diagnostic or therapeutic procedures that require an artificially created access tract. For example, the embodiments described herein may be used in many urological applications (e.g., the removal of ureteral strictures and stones, the delivery of drugs, RF devices and radiation for cancer treatment, etc.). In such applications, the percutaneous access sheath 100 may have a length of about 30-300 cm with an unexpanded diameter of about 7-20 French and an expanded diameter of about 14-60 French. The sheath 100 may also be used in many gastrointestinal applications, which require the introduction of a surgical retractor (e.g., to the removal gallstones and appendix procedures). In such applications, the percutaneous access sheath 100 may have a length of about 10-50 cm with an unexpanded diameter of about 3-15 French and an expanded diameter of about 15-60 French. The percutaneous access sheath 100 may also be used as an access catheter for many gastrointestinal applications (e.g., colon therapies, esophageal treatment and the treatment of bowel obstructions). In such applications, the percutaneous access sheath 100 may have a length of about 30-300 cm with an unexpanded diameter of about 7-40 French and an expanded diameter of about 14-120 French.

The sheath may also be used in many cardiovascular applications (e.g., to provide access for minimally invasive heart bypass, valve replacement or the delivery of drugs or angiogenesis agents). In such applications, the percutaneous access sheath 100 may have a length of about 30-300 cm with an unexpanded diameter of about 3-12 French and an expanded diameter of about 5-30 French. For vascular applications (e.g., minimally invasive access to the aorta or contralateral leg arteries for the treatment of, for example, an abdominal aortic aneurysm), the percutaneous access sheath 100 may have a length of about 30-300 cm with an unexpanded diameter of about 5-30 French and an expanded diameter of about 15-75 French. For gynecological applications (e.g., endometrial therapies, delivery of drugs, delivery of cancer agents, sterilization procedures, etc.), the percutaneous access sheath 100 may have a length of about 10-100 cm with an unexpanded diameter of about 3-20 French and an expanded diameter of about 6-60 French.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A method of providing percutaneous access, said method comprising:
   making an incision through skin;
   inserting a guidewire through the incision in the skin and into or through the renal collection system,
   percutaneously inserting a circumferentially continuous elongate tubular structure through the incision in the skin and over the guidewire and into the renal collection system, the elongate tubular structure comprising a distal region, a proximal region, and a tapered region between the distal region and the proximal region, the distal region having a first, folded, smaller cross-sectional profile and the proximal region having a second, greater cross-sectional profile;
   inflating a balloon that is positioned within an interior lumen of said folded distal region of said elongate tubular structure to expand and unfold said distal region of said elongate tubular structure radially around its longitudinal axis from said first, smaller cross-sectional profile to said second, greater cross-sectional profile;
   releasing the elongate tubular structure from a constraining tubular jacket, the constraining tubular jacket sharing the same longitudinal axis as the elongate tubular structure, wherein releasing the elongate tubular structure from the constraining tubular jacket comprises tearing said constraining tubular jacket along a perforation; and
   removing said balloon from said distal region of said elongate tubular structure to open the interior lumen in said elongate tubular structure, the interior lumen open to an external environment outside the skin on its proximal end and open to the renal collection system on its distal end.

2. The method of claim 1, wherein the inflating a balloon is accomplished using a balloon catheter positioned within the interior lumen of the distal region of the elongate tubular structure.

3. The method of claim 1, wherein the inflating a balloon comprises radially expanding said balloon.

4. The method of claim 1, further comprising the step of separating said constraining tubular jacket from said elongate tubular structure.

5. A method of providing percutaneous access, said method comprising:
   making an incision through skin;
   inserting a guidewire through the incision in the skin and into or through the renal collection system,
   percutaneously inserting a circumferentially continuous elongate tubular structure through the incision in the skin and over the guidewire and into the renal collection system, the elongate tubular structure comprising a distal region, a proximal region, and a tapered region between the distal region and the proximal region, the distal region having a first, folded, smaller cross-sectional profile and a beveled distal tip, the proximal region having a second, greater cross-sectional profile;
   inflating a balloon that is positioned within an interior lumen of said folded distal region of said elongate tubular structure to expand and unfold said distal region of said elongate tubular structure from said first, smaller cross-sectional profile to said second, greater cross-sectional profile;
   releasing the elongate tubular structure from a constraint, the constraint sharing the same longitudinal axis as the elongate tubular structure, wherein releasing the elongate tubular structure from the constraint comprises tearing said constraint along a perforation; and
   removing said balloon from said distal region of said elongate tubular structure to open the interior lumen in said elongate tubular structure, the interior lumen open to an external environment outside the skin on its proximal end and open to the renal collection system through said beveled distal tip.

6. The method of claim 5, wherein the inflating a balloon is accomplished using a balloon catheter positioned within the interior lumen of the distal region of the enlongate tubular structure.

7. The method of claim 5, wherein the inflating a balloon comprises radially expanding said balloon.

8. The method of claim 5, further comprising the step of separating said constraint from said elongate tubular structure.

9. A method of providing percutaneous access, said method comprising:
   making an incision through skin;
   inserting a guidewire through the incision in the skin and into or through the renal collection system,
   percutaneously inserting a circumferentially continuous elongate tubular structure over the guidewire and into the renal collection system, the elongate tubular structure comprising a distal region, a proximal region, and a tapered region between the distal region and the proximal region, the distal region having a first, folded, smaller cross-sectional profile and the proximal region having a second, unfolded, greater cross-sectional profile;
   inflating a balloon that is positioned within an interior lumen of said folded distal region of said elongate tubular structure to expand and unfold said distal region of said elongate tubular structure from said first, smaller cross-sectional profile to said second, greater cross-sectional profile;
   releasing the elongate tubular structure from a constraining tubular jacket, the constraining tubular jacket sharing the same longitudinal axis as the elongate tubular structure, wherein releasing the elongate tubular structure from the constraining tubular jacket comprises tearing said constraining tubular jacket along a score line; and removing said balloon from said distal region of said elongate tubular structure to open the interior lumen in said elongate tubular structure, the interior lumen open to an external environment outside the skin on its proximal end and open to the renal collection system on its distal end.

10. The method of claim 9, wherein the inflating a balloon is accomplished using a balloon catheter positioned within the interior lumen of the distal region of the enlongate tubular structure.

11. The method of claim 9, wherein the inflating a balloon comprises radially expanding said balloon.

12. The method of claim 9, further comprising the step of separating said constraining tubular jacket from said elongate tubular structure.

13. A method of providing percutaneous access, said method comprising:
  making an incision through skin;
  inserting a guidewire through the incision in the skin and into or through the renal collection system,
  percutaneously inserting a circumferentially continuous elongate tubular structure through the skin over the guidewire and into the renal collection system, the elongate tubular structure comprising a distal region, a proximal region, and a tapered region between the distal region and the proximal region, the distal region having a first, folded, smaller cross-sectional profile and a beveled distal tip, the proximal region having a second, greater cross-sectional profile;
  inflating a balloon that is positioned within an interior lumen of said folded distal region of said elongate tubular structure to expand said distal region of said elongate tubular structure from said first, folded, smaller cross-sectional profile to said second, greater cross-sectional profile;
  releasing the elongate tubular structure from a constraint, the constraint sharing the same longitudinal axis as the elongate tubular structure, wherein releasing the elongate tubular structure from the constraint comprises tearing said constraint along a score line; and
  removing said balloon from said distal region of said elongate tubular structure to open the interior lumen in said elongate tubular structure, the interior lumen open to an external environment outside the skin on its proximal end and open to the renal collection system through said beveled distal tip.

14. The method of claim 13, wherein the inflating a balloon is accomplished using a balloon catheter positioned within the interior lumen of the distal region of the enlongate tubular structure.

15. The method of claim 13, wherein the inflating a balloon comprises radially expanding said balloon.

16. The method of claim 13, further comprising the step of separating said constraint from said elongate tubular structure.

17. A method of providing percutaneous access, said method comprising:
  making an incision through skin;
  inserting a guidewire through the incision in the skin and into or through the renal collection system,
  percutaneously inserting a circumferentially continuous elongate tubular structure through the incision in the skin over the guidewire and into the renal collection system, the elongate tubular structure comprising a distal region, a proximal region, and a tapered region between the distal region and the proximal region, the distal region having a first, folded, substantially continuous, smaller cross-sectional profile, the proximal region having a second, unfolded, greater cross-sectional profile;
  inflating a balloon positioned within an interior lumen of said folded distal region of said elongate tubular structure to expand and unfold said distal region of said elongate tubular structure from said first, folded, substantially continuous, smaller cross-sectional profile to said second, unfolded, greater cross-sectional profile; and
  removing said balloon from the interior lumen of said distal region of said elongate tubular structure to open the interior lumen in said elongate tubular structure, the interior lumen open to an external environment outside the skin on its proximal end and open to the renal collection system on its distal end.

18. The method of claim 17, wherein the inflating a balloon is accomplished using a balloon catheter positioned within the interior lumen of the distal region of the elongate tubular structure.

19. The method of claim 17, wherein the inflating a balloon comprises radially expanding said balloon.

* * * * *